(12) United States Patent
Rittman, III et al.

(10) Patent No.: US 6,451,015 B1
(45) Date of Patent: Sep. 17, 2002

(54) METHOD AND SYSTEM FOR MENU-DRIVEN TWO-DIMENSIONAL DISPLAY LESION GENERATOR

(75) Inventors: William J. Rittman, III, Lynnfield, MA (US); Way Yin, Bellingham, WA (US); Eric R. Cosman, Jr.; Eric R. Cosman, both of Belmont, MA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/195,118

(22) Filed: Nov. 18, 1998

(51) Int. Cl.⁷ .............................................. A61B 18/18
(52) U.S. Cl. ............................ 606/34; 606/41; 600/523
(58) Field of Search .......................... 128/920; 600/523, 600/525; 607/98, 99, 101, 102, 105; 606/32, 34, 37–42, 45, 49

(56) References Cited

U.S. PATENT DOCUMENTS

| | | | |
|---|---|---|---|
| 5,233,515 A | | 8/1993 | Cosman |
| 5,820,568 A | | 10/1998 | Willis |
| 5,868,737 A | * | 2/1999 | Taylor et al. ................. 606/34 |
| 5,871,481 A | * | 2/1999 | Kannenberg et al. ......... 606/34 |
| 6,014,581 A | | 1/2000 | Whayne et al. |
| 6,056,745 A | | 5/2000 | Panescu et al. |
| 6,123,702 A | | 9/2000 | Swanson et al. |

\* cited by examiner

*Primary Examiner*—Rosiland S. Kearney (57) ABSTRACT

A high frequency generator system with a computer graphic two-dimensional user-interactable interface is achieved to allow selection of menus associated with the function, state, and output parameters of the high frequency generator system. A two-dimensional graphics display is coupled directly or remotely to a high frequency power source system which is further connected to electrodes in contact or proximity to the tissue of a patient's body. A two-dimensional display allows the user to see, in a compact, convenient, and comprehensive way, selection menus for use of the high frequency generator system, control of its parameters, monitoring of its processes during clinical application, and graphics displays related to historic or current image scan data and real-time monitoring of output parameters related to the application. Pre-set or user-selectable arrays of parameters can be selected through the two-dimensional user interface to the high frequency generator system. Real-time plotting of single or multiple output parameters as a function of time course during the clinical application can be graphically displayed on the two-dimensional display. Digital displays, alphanumeric streams of information, help menus, prompts, and sequences of menus may be selected by the two-dimensional interface through actuators on the interface or on the panel of the high frequency generator system. Several forms of the interface, user actuators, screen layouts, and methods for use of this system accommodate the specific objectives.

6 Claims, 7 Drawing Sheets

METHOD AND SYSTEM FOR MENU-DRIVEN TWO-DIMENSIONAL DISPLAY LESION GENERATOR

FIELD OF THE INVENTION

This invention relates generally to the advancement of medical technology, processes, and systems for the treatment of pain, neurological disorders, cancer, and other clinical maladies. More particularly, this invention is directed at a method and system for producing therapeutic lesions or tissue alterations by means of a high frequency generator and electrodes, including a two-dimensional computer graphics menu interface. A two-dimensional display is combined and/or connected to a generator that produces a high frequency electrical output. The generator output is in turn connected to an electrode system which is in contact with the patient's body to deliver a therapeutic electrical signal. The two-dimensional user interface has menu functions which the operator can interact with to control or monitor the process of the clinical procedure. Interactive selection of parameters associated with the two-dimensional computer display and output of the high frequency generator functions clarify the process to the user and increase convenience and safety. Various specific embodiments of the two-dimensional computer graphic menu display accommodate the specific clinical applications and designs.

BACKGROUND TO THE INVENTION

The use of radiofrequency and high frequency generator systems which deliver electrical output to electrodes that are connected to a patient's body is known in the clinical literature and art.

By reference, examples of radiofrequency heat lesion generators used in clinical practice are the RFG-3C Generator (produced by Radionics, Inc., Burlington, Mass.) and the N-50 High Frequency Generator (produced by Leibinger GmbH, Freiburg, Germany).

Typical controls for existent high frequency generators include knobs, push buttons, selection buttons for modes, and real-time, two-dimensional graphics display of generator output parameters such as tissue temperature, voltage, power, current, impedance, etc. By way of reference, U.S. Pat. No. 5,233,515, entitled Real Time Graphic Display of Heat Lesion Parameters in a Clinical Lesion Generator System describes use of a two-dimensional graphic display of lesion parameters.

The above-referenced model RFG-3C Heat Lesion Generator and N-50 Lesion Generator, which are commercially available units, have built-in digital display of parameters such as impedance, temperature, power, etc. They also have LCD displays built into their front panels which can display the status of functions of the generator, mode of operation such as stimulator, lesion, impedance, etc. The LCD displays consist of one or several alphanumeric lines of characters related to the above-mentioned functional or output characteristics of the generator. Other push buttons and knobs on the panel of these lesion generators select the functional modes of the generator output and, according to those functional modes, set graphic alphanumeric displays can appear on the liquid crystal display in one-dimensional alphanumeric strings.

SUMMARY OF THE INVENTION

The present invention is directed to a method and system for a high frequency generator and electrode system for clinical therapy which includes a two-dimensional computer graphic display with menu information and user interactive adaptions. The user is able to input parameters associated with the two-dimensional display and observe multiple alphanumeric lines of display parameters as well as two-dimensional, real-time graph displays of parameter values during a clinical procedure. Customized sequences of parameters, application-specific parameter sets, and pre-set parameter values of commonly used inputs can be stored in the system and recalled using the two-dimensional, menu-driven display. A user may choose particular selections of menu modes, data entry, and output graphics which can be selectively input into the system. The advantages of the present system and method reside in part in the combined clarity, efficiency, and interactability of the two-dimensional computer graphic menu style interface in combination with the high frequency generator.

In accordance with one embodiment to the present invention, a two-dimensional liquid crystal display (LCD) is built into the front panel or connected in conjugation with a high frequency generator station. A range of two-dimensional displays in the form of menus and graphic representations enable a user to select parameters, modes, and pre-set application parameter sets by pushing buttons that are encoded to the interface display. The user may interact with the display by selecting icons, associated push buttons, associated level knobs, or keyboard connections. Data may be input and displayed into the two-dimensional graphics interface. Graphical plots of the high frequency generator output as a function of time can be selected and displayed on the LCD screen.

In contrast to the previous high frequency generator systems described above, the present invention enables the user to input information and display it on the two-dimensional graphics. Input of a procedure type, saving parameters, the saving of the data parameter stream for a procedure, the input of the patient's name, other patient history and legal documentation are possible embodiments of the present invention. For example, the user can enter the patient's name, the type of procedure, and a set of favorite parameters into the system. This information may then be stored in the generator or associated computer, to be selected by user-activated enablements connected to the display.

The present system and method has the further advantage of allowing the user to observe and interact with one simplified two-dimensional display generator and associated application parameters, and to visualize these parameters as the procedure goes forward. The present technique has the advantage of simplifying the process of treatment control and clarifying, at every step in a visual display, the generator output and the electrode performance. The present invention has the further advantage of saving time and possible errors during the procedure by presenting a clearer visual output, a simplified set of visual and control options, and a less awkward and inconvenient interface as compared to many prior high frequency generator systems.

The existent lesion generator systems described above do not have a two-dimensional graphics display integrated with a computer and a high frequency generator which provides two-dimensional graphing functions based on the output of the generator. Nor do they provide user interactable menus and functional positions to monitor, control, and select the functions of the generator. This limitation of existing generators presents an inconvenience to the user, since they do not provide a single visible two-dimensional graphics display which displays the modes of the generator, and allows the operator to select modes and to interactively input parameters associated with the function of the generator and its clinical application. Further, the above-mentioned generators do not have two-dimensional displays to enable the user to observe in one graphics display options of several mode selections at one time or to see alphanumeric strings of information, status displays, help lines, and menus. Nor do they provide two-dimensional graphic representations of the generator function, control, or output in one computer graphic user interface. Therefore, the information available to the user is limited in above-mentioned lesion generator systems. Accordingly, it is an object of the invention to provide a lesion generator system with a computer graphic user interactable, menu-driven interface that avoids these limitations of lesion generator designs.

Generally, present lesion generator systems require the operator to set parameters on digital or analog displays and/or knob or switch positions. There is no provision for storing parameters related to a particular procedure which has been used successfully before by the clinician. Accordingly, it is an object of the invention to provide selectable application-specific parameters for a lesion generator system to save time and to assure reproducibility of parameter settings for similar clinical applications.

Lesion generator systems such as those referred to above require specific attention by the clinician or his technician to set parameters by knobs or switches and to watch several digital meter displays at several locations on the generator panel as the operation proceeds. It is thus an object of the invention to provide a more simple and consolidated display for setting up a particular procedure and monitoring its course during patient application. A simplified, user interactable interface both saves valuable time in the procedure and reduce the chance of errors being made by lack of attention to specific and multiple generator output displays.

For the reasons described above, a high frequency generator system for lesion making having a menu-driven, user-interactive, two-dimensional graphics display has practical and clinical advantages. Accordingly, an effective display of this type built into a high frequency clinical generator and electrode system is desirable for the purposes of safety, convenience, efficiency, and consistency of clinical results.

These and other features and advantages of the present method and system will become apparent upon reference to the detailed description that follows.

BRIEF DESCRIPTION OF THE DRAWINGS

In the drawings, which constitute a part of the specification, embodiments exhibiting various forms and features hereof are set forth, specifically.

DETAILED DESCRIPTION OF THE INVENTION

Figure 1:
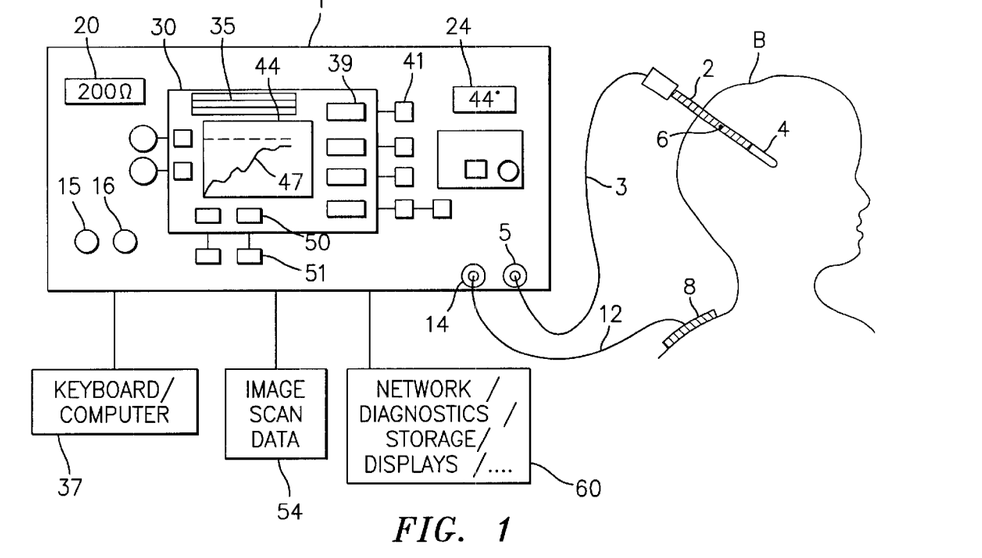
FIG. 1 is a schematic diagram showing one embodiment of a high frequency generator system according to the invention with computer connection, two-dimensional user interactive interface, and connection to an electrode system applied to a patient.

Referring initially to FIG. 1, one embodiment of a system constructed and operated in accordance with the present invention comprises a high frequency generator system 1 connected to a therapeutic electrode 2 which is inserted into or is in contact with a patient's body B. Connection is made between the generator system 1 and electrode 2 by connection cable 3. An exposed electrode tip 4 for the electrode enables conductive communication with the patient's tissue and the application of output from the generator through connection jack 5 to perform a therapeutic lesion or alteration of bodily tissue. In addition, a reference electrode 8 is applied to the patient's body and connected by connection 12 to a secondary jack output 14 on the generator system 1.

The generator system 1 includes a source of high frequency output, such as a radiofrequency power supply. This will provide, for example, a high frequency voltage on the exposed electrode tip 4 to create a heat lesion, pulsed radiofrequency modification, or stimulative response of patient tissue.

By reference, information on high frequency generator systems can be found in the review article entitled "Methods of Making Nervous System Lesions" by E. R. Cosman and B. J. Cosman, in Wilkins R H, Rengachary S S (eds): *Neurosurgery.* New York: McGraw-Hill, 1984. Vol. III, pp. 2490–2498. Radionics, Inc. of Burlington, Mass., and Leibinger GmbH of Freiburg, Germany, provides information on high frequency generating systems. By reference, examples of connections of generator systems such as 1 to electrode systems such as 2 are described in the above-mentioned references.

Various controls on the generator system such as knobs 15 or push buttons 16 are present. In addition, digital output displays 20 for impedance or display 24 for temperature as measured at the electrode tip 4 are present.

In the disclosed embodiment of the invention, generator system 1 includes a two-dimensional display 30. In one embodiment, the display includes a pixel-based screen. Each of the pixels may be individually addressable, for example, using bit mapped or raster scan techniques. Typically, the screen incorporates over 100 pixels in two orthogonal directions.

The two-dimensional display 30 thus provides a variety of display items and user selection icons including graphical images and text-based information. For example, it may have multi-line alphanumeric display capability 35 to display generator system status, output parameters, help menus, and input from the user. The clinician may input the patient's name via a keyboard and/or computer 37 and have it displayed on display element 35 as part of the two-dimensional computer graphic display 30. Various option icons, illustrated by the column of blocks such as 39 indicate selectable options. The options could be parameters, mode selections, menu selections, application parameter sets, and so on. These can be selected or activated by the neighboring push button or knobs, illustrated for example by button 41 on the generator system panel associated with icon 39 on the two-dimensional display. A variety and multiplicity of icon and associated control buttons can be arranged around the two-dimensional display, as illustrated by other elements such as icon 50 and control element 51.

The two-dimensional display, as illustrated in FIG. 1, also includes a two-dimensional plotting or functional graphics display window 44. Window 44 may, for example, display a graph 47 of a lesion output parameter as a function of time. For example, this could be the impedance, electrode tip temperature, power, or other output parameter value, or measured value, from the generator system 1, plotted as a function of time or plotted as a function of other parameters. Multiple graphs could be displayed in such a graphical display screen 44, or historic or standard graphs stored in memory could be displayed for reference or comparison.

In accordance with the present invention, image scan data illustrated by block 54 from an image scanning machine such as a CT, MR, PET, X-ray or other scanning modality may be used as input into the generator system. This input may be displayed also on the graphics display 44 in various sections, three-dimensional (3-D) renderings, reconstructions, outlines, segmentation, etc. A display of the electrode position with respect to such anatomical graphics from image data or renderings of image data may be displayed on the two-dimensional display 44. Effects of a preplanned calculation of the effect of the generator output, such as heat lesion isotherms, pulse radiofrequency effects, or stimulation ranges may be calculated in the system and displayed on the display 44.

The generator system may also be connected to a data network, other diagnostic imaging or input devices, data storage means, or other ancillary displays as illustrated by block 60. For example, patient information network, website connection, Ethernet, or tele-medicine networks can be connected to generator system 1 for display or patient's call-up of information on the 2-D interface 30. Diagnostic, drug, or history information from the patient's record may also be brought in and displayed in the same way. The high frequency procedure may be stored on a data file for permanent record or can be transmitted by tele-medicine or video lines to other systems by element 60. Computer graphic display 30 may be a user interface analogous to or integrated with a website computer interface for such communication between the clinical application of the generator system 1 and a broader network of computer or information systems. Icons such as 39 may control the transmission and transformation of such information at the user's command.

Figure 2:
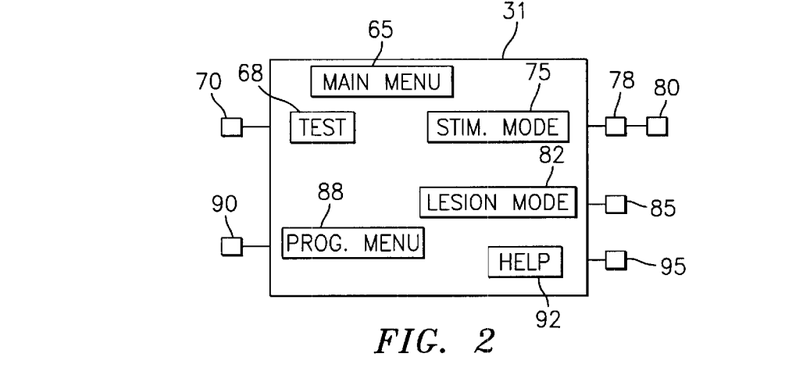
FIG. 2 illustrates an embodiment of a two-dimensional interface display in accordance with the present invention.

FIG. 2 shows a diagram illustrating a display menu which could be shown on the graphics display 30 of FIG. 1. The graphic display screen is illustrated by 31 in FIG. 2, and represents an analogous graphics display parameter 30 as in FIG. 1. The alphanumeric display 65 may indicate that it is a main selection menu and has various other alphanumeric information about the nature of the menu and its use. The menu may have a multiplicity of selection options. An example is an icon 68 related to test functions. This may be activated or accessed by associated button, actuator, or knob 70 on the front panel of the system 1. Alternatively, 70 may represent a keyboard or other control element that relates to test functions 68. Pressing or actuating element 70 may bring the two-dimensional user interface 30 to a test function menu, which may have a sub-menu of its own related to testing and diagnostic functions for the system. Similarly, a stimulation mode icon 75 may be an option on two-dimensional display 31. It may be actuated or controlled by one or more switches, buttons, levers, etc. such as elements 78 and secondary element 80. Elements may be actuated in series or parallel to achieve a prescribed effect on the menu, choice of sub-menu, or choice of other parameters or options. Similarly, other selections of modes, such as lesion mode icon 82 with associated actuator 85, or access may be selected. A program menu which is more general, illustrated by icon 88, may be accessed by push button 90. Help menus, illustrated by icon 92 may be accessed, controlled, or selected by selector element 95.

The user, according to the present invention, has the capability in generator system 1 of FIG. 1 to access and interact with various icons, symbols, and mode selections, graphically displayed in two-dimensional display 30. These displays may be simultaneously represented on display 30 by its multi-icon, multi-windowed, two-dimensional region of interest.

Figure 3:
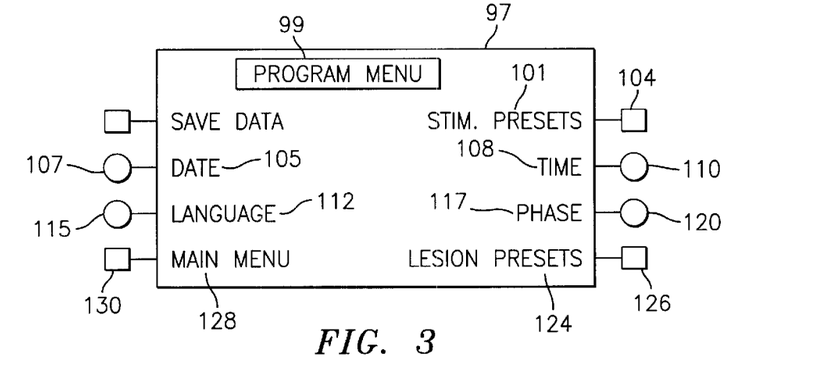
FIG. 3 illustrates one embodiment of a two-dimensional menu display in accordance to the present invention.

FIG. 3 illustrates another example of a two-dimensional menu display 97. This may be designated in alphanumeric display 99 as a program menu involving numerous generator inputs, outputs, functions, or modes. As an illustration, stimulator pre-set ranges are illustrated by alphanumeric descriptor 101. It may be accessed, rastered through, or scrolled by knob or button element 104. Date display 105 can be actuated by element 107. Setting of the time 108 may be set and manipulated by actuator 110. Various language options for generator display are illustrated by icon 112 and selected by actuator 115. The phase or mode of the generator may be changed by icon 117 being selected by the user with element 120. Various lesion presets may be directed to sub-menus by icon 124 and rastered through element 126. Alternate menus such as main menus or sub-menus can be accessed by branching streams through icon 128 and access element 130.

An advantage of such a program menu as in FIG. 3, in accordance with the present invention, is the obvious single glance display for the user of many menu possibilities, and access to these possibilities by active interaction of the user with the two-dimensional interface. As with the Windows environment from the NT operating system, such icons provide a clear and simple pathway for the user to enter the environment of the generator system 1. It leads the user in an obvious common sense and logical fashion to a complex of controls which otherwise would be difficult to visualize, but are easily visualizable on a two-dimensional, menu-driven computer graphics display in accordance with the present invention. In the present day environment of PC computers and Window interfaces, such an adaption for a generator system provides a user-friendly and simplified method of controlling a complex process such as the control of a high frequency generator and electrode system in accordance with the present invention.

Figure 4:
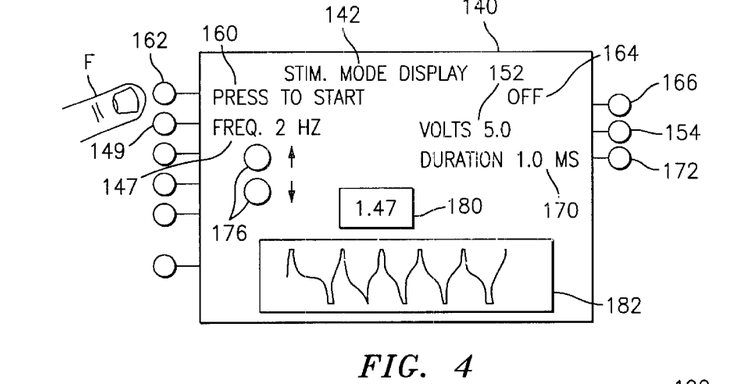
FIG. 4 shows another embodiment of a two-dimensional display according to the present invention.

FIG. 4 illustrates another embodiment in accordance with the present invention of a two-dimensional user display 140. This may be designated as a stimulator mode display indicated by icon 142. The user may be prompted to control the frequency, illustrated by icon 147, through knob, raster, or button control 49, or may be prompted to vary the voltage of the stimulator output, illustrated by icon 152 and controlled by element 154 on the generator system panel. An alphanumeric icon 160 suggests the beginning of a stimulator process which is actuated by push button 162 under digital control by the patient's finger F. Cessation of stimulation may be illustrated by icon 164 and actuated by button 166 on the generator panel. Other parameter controls such as the duration of pulses 170 may be controlled by element 172. Buttons/knobs associated with raster elements 176 may control stimulator voltage which, in turn, may be illustrated by a large and evident digital display 180. The two-dimensional graphic output of stimulator voltage or current may be plotted as a function of time on a sub-graphics display 182. Graphics display 182 may be a real-time, high resolution, two-dimensional plot of a stimulator output, such as voltage or current, as a function of time. Other controls may enable freezing and storage of such waveforms or variation of the waveform itself by control element.

An advantage of the display in FIG. 4 in accordance with the present invention is a view-at-a-glance interface which is user interactable, having both alphanumeric and real-time graphic display to present full control to the operator at each instance over a critical clinical implementation such as stimulation testing of a patient during or prior to an ablative or tissue modifying high frequency procedure. Such a display gives assurance and quality assurance to a user. The clarity of its presentation, with all parameters displayed and active, is analogous to the displays in the cockpit of an airplane where the pilot, who is analogous to the surgeon, can see all critical parameters at a glance in a highly graphic and holistic manner.

Figure 5:
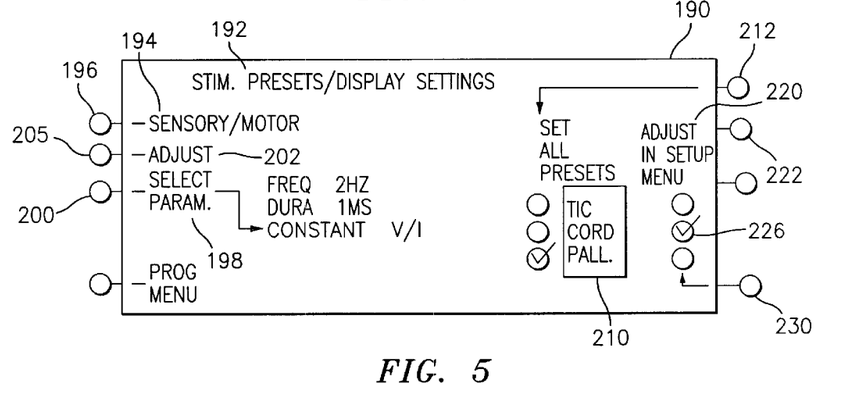
FIG. 5 shows another embodiment of a display with menu selections in accordance with the present invention.

FIG. 5 illustrates another embodiment in accordance with the present invention where the graphics display 190 indicates that various stimulator preset or display settings indicated by icon 192 will be present on the 2-D user interface. For example, the user may select either sensory or motor stimulation modes, illustrated by icon 194 and selectable by button 196. Parameter selection is illustrated by icon 198 and selected by element 200. Adjustment of the parameters may be signaled by icon 202 and selected by button 205. The selection of a clinical procedure such as a TIC procedure for trigeminal nerve pain, or a percutaneous cordotomy for intractable pain, or a pallidotomy for movement disorders may be illustrated and selected by icon 210 and by a raster push button 212 which can scroll through a variety and an indefinite number of pre-set or canned procedure parameter sets. These parameter sets may be those that are common as a standard in the clinical literature or experience, or there may be parameter sets which have been chosen by the individual user according to his experience and which is appropriate for a clinical application for a particular patient. The parameter sets for a given procedure can be modified according to an adjustment icon 220, or a new procedure can be entered by a keyboard. Parameters for that procedure can be selected and adjusted by control elements 222. This selection and adjustment may consist of alphanumeric input by the clinician of a new procedure type, a new set of parameters for that procedure, and storage of these procedures within the generator system as controlled by the 2-D user display and according to icons and check rasters 226 and raster control 230. The advantage of the embodiment of FIG. 5 in accordance with the present invention is the ability of the user to interactively set up new realms of parameter controls and parameter sets according to his clinical experience and to visualize and access these modes at will by the 2-D user interface and control buttons.

Figure 6:
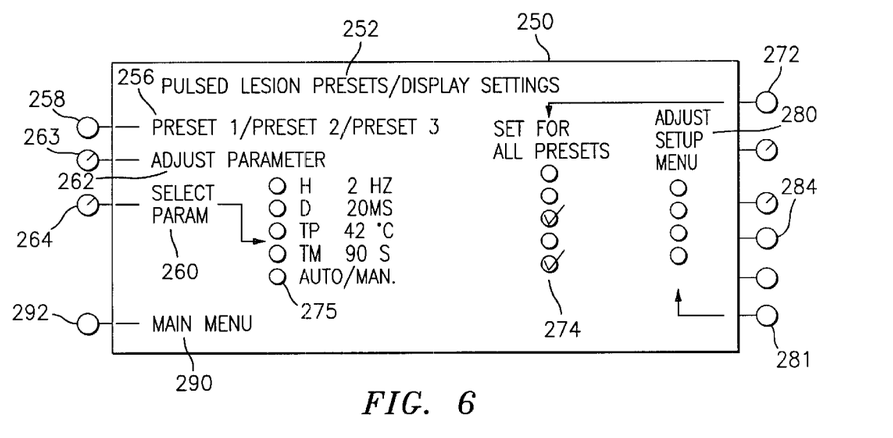
FIG. 6 shows one embodiment of a lesion display and menu options in accordance with the present invention.

FIG. 6 shows another embodiment of the present invention in which the two-dimensional menu display 250 presents a user option for making thermal or non-thermal neurological lesions. This might be applicable during pain procedures, movement disorder procedures, or other neurological interventions in which discrete heat destruction of neural structures or neural modification is to be achieved. Examples of such procedures are described in the reference by Cosman, et al. given above. Alphanumeric line 252 describes the choice of the 2-D display related to pulsed lesion pre-set parameters, and various display settings and options. Alphanumeric lines 256 refer to various pre-set parameter groups which the surgeon may have stored in the computer related to the display. These may be selected by actuator 258. In the column 274, a range of pre-set groups is displayed and accessed by button 272, which may raster a checkpoint down the column of parameter pre-sets. Adjustment of the parameters can be made by actuator 281 and variation of pre-set menus and parameter selections can be chosen thereby, as displayed by icons in column 280. Adjustment of individual parameters can be made by a set of knobs, buttons, raster actuators, etc., as illustrated by element 284. Selection of the pulsed characteristics for a radiofrequency wave train, as is used in pulsed radiofrequency neural alteration, can be adjusted by knob 263 as indicated by icon 262. The parameters to be adjusted can be selected, as indicated by icon 260, and selection can be made by adjustment 264. Display and adjustment of parameters such as pulse frequency, pulse duration, set temperature for the lesion, and time are indicated by the icon displays H, D, TP, and TM with corresponding, adjacent, numerical values, as shown in FIG. 6. Various automatic sequencing of parameters of control may be selected by the auto/man button indicated by 275 in FIG. 6. The computer may be pre-programmed to perform automatic sequences of generator output application or may be controlled directly by the surgeon via a manual knob, push button, or lever to meter out levels of generator output parameters as applied to the patient's tissue. Escape from this pre-set selection menu may be done or prompted by icon 290, which is actuated by button 292 to return to a main menu or other menus, as described above previously.

One advantage of the embodiment as shown in FIG. 6 is that the user can interactively choose pre-set parameter values for an application and store the parameters for further similar clinical applications. A further advantage is that the parameter arrays are visible in a simplified, single, two dimensional display. The display can be interacted with by applicator elements on the generator system. New pre-set parameter values for lesioning or pulsed radiofrequency or electromagnetic field application can be chosen and further stored, leading to flexibility and changeability of the menu selections by the user, as opposed to pre-packaged menus supplied by the factory.

Figure 7:
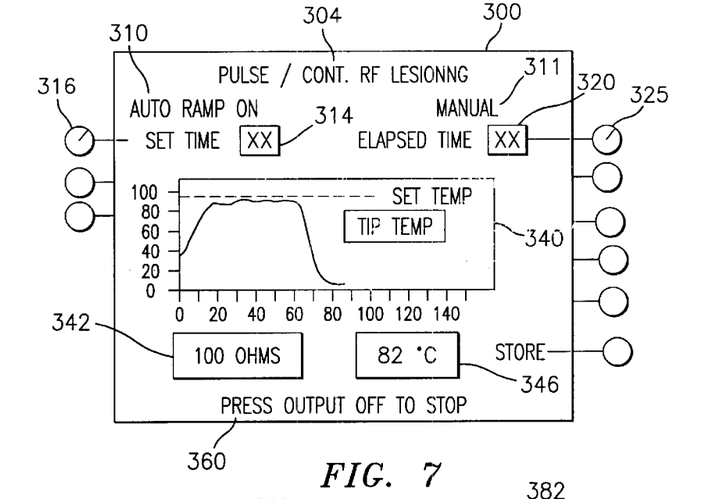
FIG. 7 shows one embodiment of a two-dimensional, time-dependent graphics readout with user interaction in accordance with the present invention.

In another embodiment of the invention, FIG. 7 shows a two-dimensional screen display 300 in association with the high frequency generator system. The display illustrates use of real-time graphics together with alphanumeric controls and readout. Icon 304 indicates a selection of either pulsed or continuous radiofrequency output for producing tissue modification. The user has interactive selections such as icon 310 (corresponding effector not shown) which selects a choice of ramp-up of output level to a set or predetermined level. Alternatively, icon 311 (corresponding effector not shown) can be selected, and the user can ramp the output up to desired levels via manual control. Icon 314 is a set time indicator which can be actuated by effector 316. Other input parameters such as temperature may be defined in a similar manner. Icon 320 reads out the selectable elapsed time of high frequency exposure determined by effector 325. When the application of high frequency output is commenced, a real-time, two-dimensional graphics display of one of the output or lesioning parameters may be expressed as a function of time, as illustrated by graphic readout 340. This illustrates, as one example, the tip temperature of an electrode in contact with the patient's tissue. Temperature sensors 6 in the electrode may detect the temperature of nearby tissue, and this is measured as part of the high frequency system 1 in FIG. 1. Electronic data associated with said measurements can then be stored and represented in real time as a function of time, as illustrated by the graph in two-dimensional display 340, which is part of the overall two-dimensional menu display 304. One or more of such real-time graphs can be displayed. They may be overlaid on the same coordinate axes and differentiated by various graphic methods, such as line width, line character, line color, and so on. Set temperature levels at various points can also be displayed and selected by menu on the graphics display. In addition, digital readout of high frequency parameters may also be shown. Window 342, for example, displays a digital readout of the impedance measured from the electrode in the patient's tissue. The tip temperature or temperature of a satellite electrode (not shown) to monitor surrounding tissue is displayed in window 346. Help menus or prompt menus can be displayed in alphanumeric form such as icon or line 360, which indicates to the user how to terminate the procedure when the desired clinical result has been reached.

FIG. 7 illustrates an advantage of the present invention which is that the two-dimensional user interactive display can provide a multiplicity of crucial information to the clinician during procedure. This information can include prompts, selection, control parameter information, as well as real-time dynamic graphics of lesion parameters plotted as a function of time for instant visualization. For example, rapid overshoots or erratic behavior of the temperature as function of time are immediately visible from a graphics display such as 340. A hazard of radiofrequency heat lesion generation is that the tissue temperature can run away to the boiling point causing charring, boiling, tissue explosion, and other highly undesirable and uncontrolled effects. By a graphics display such as that shown in 340 in accordance with the present invention, together with digital displays such as 342 and 346, all in one compact user-interactable interface, hazards such as tissue boiling and charring can be avoided.

Also referring to FIG. 7 and in accordance with the present invention, other graphics displays with real-time or stored two-dimensional graphic plots accommodate desired clinical adaptions. For example, a variety of two-dimensional graphic displays of generator parameters, temperature sensors, or multiple temperature sensor readouts could be shown in FIG. 7 in a graphics display such as that in FIG. 7. Simultaneous plots of temperature, power, current, voltage, impedance, multiple temperature sensing temperature plots, temperature sensing for multiple temperature sensors in a single or multiple electrodes, can be plotted and graphed according to clinical application. Stored graphics displays from previous or historic applications can similarly be displayed. Display of other patient data, high frequency generator applications, standard plots or templates for graphics displays may be shown in accordance with the present invention. Multiple displays of digital or analog readouts of various types may be convenient according to the clinician's needs. Display of digital or graphical set points or thresholds, both high and low, for various output parameters may be appropriate. For example, brackets on impedance levels that are acceptable, on the high side relating to excess heating and on the low side relating to the onset of the heat lesion, may be appropriate to set for automatic cutoff or monitoring of the lesion process. Setting the high or low set points on a graphical display can trigger an automatic response of the lesion generator system. The user may interactively set such levels using the two-dimensional graphic user interface. The menu-interactive user interface has the advantage of enabling input of historical parameters, user experiential knowledge, and set points, and a unified holistic display of all of these in one graphic display.

Figure 8:
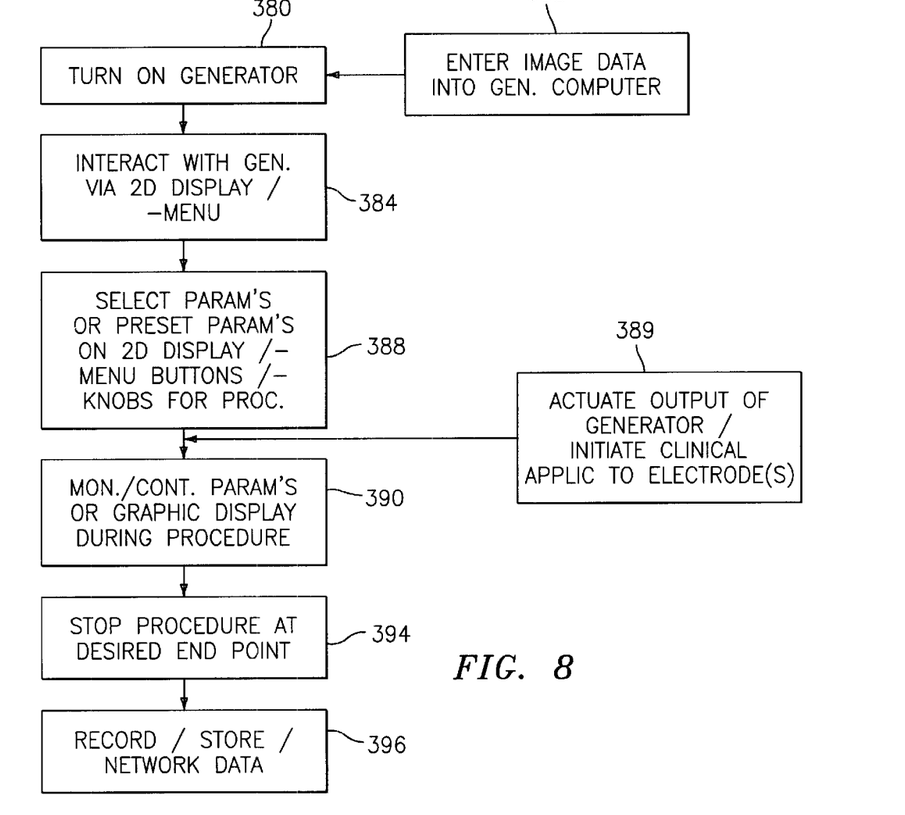
FIG. 8 shows a flow chart of one embodiment of a process employed in operating a two-dimensional user interface generator system in accordance with the present invention.

Referring now to FIG. 8, a flow chart is shown to illustrate the process of using the two-dimensional, menu-driven user interface in accordance with the present invention. It is assumed that an electrode has been placed in contact with the patient's body and connected to the generator system appropriate to a clinical procedure similar to that in the diagram of FIG. 1. The procedure thereafter starts by turning on the generator (step 380). Prior to that, or after that, entry of image data or other patient related data, or other historical procedure related data may be entered into the high frequency generator or its related computer (step 382). This may involve input of ultrasonic, CT, MR, X-ray, or other imaging data and may be done by standard media such as disc drives, tape drives, Ethernet, and so on. The user can interact with the generator system by means of a two-dimensional display and/or may select menus associated with the parameters and procedure according to the user's needs (384). The interaction with the display may include selection of application parameters for stimulation, impedance, heating, or pulsed radiofrequency, and these may be selected by a variety of actuators and associated icons on the two-dimensional display (step 388). Selection of parameters may also involve selection of patient data, manipulation of image data, visualization of electrode position in the image data, and appropriate selection of heating or stimulating parameters based on the electrode position in image data. These may be part of the step of interaction with the two-dimensional menu display (step 388). Also shown is the step (step 389) corresponding to actuation of the output of the high frequency generator to the electrode system. This step may comprise connecting the generator to the electrodes, turning on the high frequency generator, actuating a connection device to connect the output of the high frequency generator in one of its possible several modes (such as stimulation, impedance monitoring, temperature monitoring, high frequency or radiofrequency power generation) to the electrode systems. The position of step 389 in the sequence of other steps, illustrated by the embodiment of FIG. 8, may depend on the particular clinical application and judgement of the clinician. Thus the interposition of the step 389 just after step 388 can vary, and step 389 may be interposed at other points in a series of process steps in accordance with the present invention. When pre-selection of parameters and other data has been made, the step of delivering output from the generator system, such as stimulation, high frequency output for heating, pulsed high frequency output for tissue modification and so can be controlled, modulated, and monitored (step 390). This can involve observation in real time of impedance, current, voltage, power, temperature(s), visualization of modification of image data which may be being taken simultaneously in real time and inputted into the computer and generator system (step 390). The monitoring and control of the system may be enabled by visualizing the two-dimensional interactive display and modifying output parameters as needed or having automatic set levels or functional controls in the generator or displayed and set on the two-dimensional display to carry out desired functions. For example, a set of an upper temperature limit above which the operator does not wish to have the tissue temperature of the electrode rise, may enable a governance of the output power from the generator and/or turning off of the generator as appropriate. Real-time imaging input to the generator system from an imaging system may also be displayed on the two-dimensional, interactive display and decisions can be made by the operator related to the course of the procedure and variation in output parameters and cessation of the procedure (step 390). By reference, examples of measurement of parameters from a radiofrequency lesion generator system are illustrated by the lesion generator systems of Radionics, Inc. (Burlington, Mass.)

The adequacy or sufficiency of the duration, parameter levels, and other data provided to the surgeon from the generator system and the two-dimensional interactive display can enable the operator to determine if the procedure is sufficient to achieve a desired clinical result. The procedure can be stopped when it is believed that the appropriate clinical result has been achieved (step 394).

In accordance with one embodiment of the present invention, the clinician may have criteria data related to the electrode, its geometry, such as size, diameter, length, etc., the specific clinical application such as a neurological or tumor ablation procedure, and other experiential information which may be inputted into the generator system and displayed on the two-dimensional display. This data in conjugation with the data from the real-time course of the procedure may be coordinated or analyzed within the computer system or the generator system to provide indications to the operator that the procedure is going properly or improperly and/or that the procedure is adequate and should be terminated. The advantage of the two-dimensional interactive system display is that large sets of data and criteria can be visualized real time and selected and modified by the user so that complex decisions can be made easily.

In accordance with another embodiment of the invention, the data associated with the pre-selection of parameters in the course of the output application may be recorded, stored, transferred, or interactively connected by network to database systems, tele-medicine systems, website applications, or and other modern media (step 396). The data from a specific procedure may be stored within the generator system or its computer and be recallable on the user interface during repeat applications on a given patient on future applications related to other patients.

Figure 9:
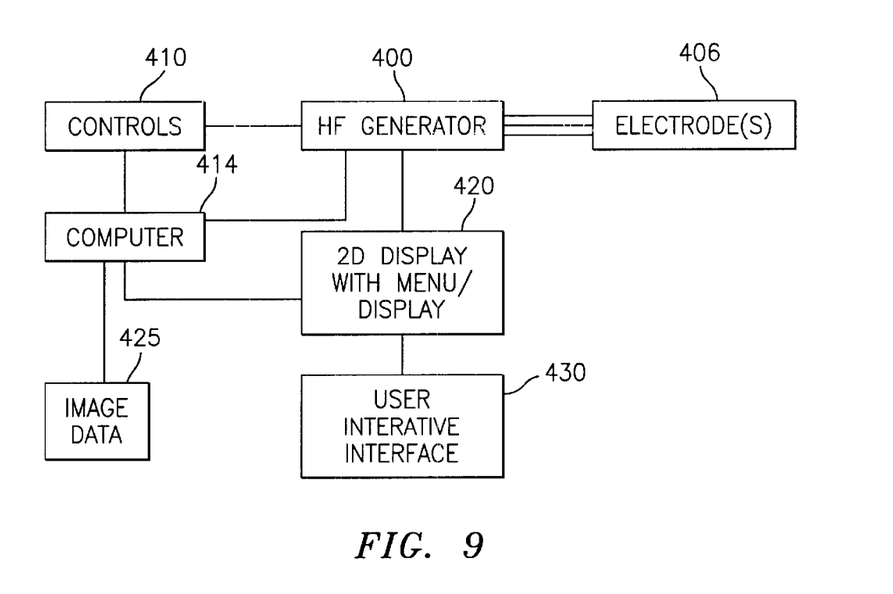
FIG. 9 illustrates a block diagram of one embodiment of a two-dimensional computer-based graphics display high voltage generator system in conjugation with electrodes and image data and controls in accordance with the present invention.

FIG. 9 illustrates another embodiment of the present invention which shows a block diagram for a system with a two-dimensional display interface. In this illustrative embodiment shown in the form of a block diagram, block 400 represents the high voltage generator system. It is understood that this may involve a complex of electrical and/or mechanical systems of different functionality. For example, it may include an electronic system with stimulative output capabilities, radiofrequency power generation capabilities, pulsed high voltage generator capabilities, microwave generators, monitoring circuitry for impedance, power, current, voltage, temperature from temperature sensors associated with the patient's body or electrodes therein, etc.

By reference, the radiofrequency generator systems of Radionics, Inc. (Burlington, Mass.) include multi-parameter output generators. Block 406 represents electrode systems connected to the generator 400 which are in contact with the tissue of the patient's body. These may include single or multiple cylindrical type, area type, reference electrode type, monopolar or bipolar electrodes, straight or curved electrodes which may be used to deliver output from the generator to the patient's tissue appropriate to the clinical procedure. The electrode systems may include or operate in conjunction with a variety of sensors for measuring temperature, impedance (e.g., sensors in the generator) and other characteristics. By reference, examples of electrode systems are given in the literature of Radionics, Inc. (Burlington, Mass.). Controls for the generator system such as knobs, switches, push buttons, raster push buttons, and so on, are illustrated in block 410.

A computer, illustrated by block 414 includes data memory to store imaging data, patient data, parameters associated with the generator and control system, and includes processing capabilities to drive, control, and/or interact with the two-dimensional display 420, with the generator 400 and, directly or indirectly, with sensors (not shown). It is appropriately connected as may be required for a particular effect to the high voltage generator 400, its control system 410, and other elements described below. For example, image data from CT, MRI, ultrasound, X-ray, or other modalities, as illustrated in block 425, may be stored historically or real time in the computer 414. A two-dimensional display system with menu selection and user interactability is illustrated by block 420. This also is connected appropriately to the high voltage generator 400 and its computer system 414. User interface software or graphic methods are displayed and cooperatively connected to the two-dimensional display 420 and is illustrated by the block 430. This may involve graphic user interface layouts to be displayed on two-dimensional display 420, and/or software that interacts with computer 414 and the controls of the generator system 410 to perform complex functions, as illustrated in the examples of the figures above. In accordance with the present invention, the user interacts with the generator system and its function through the user-interactive interface and its associated representations on the two-dimensional display.

A further advantage of the present invention is for more precise and certain control by the user over the function of the high voltage generator system. The user can visualize more easily and interact with complex functional displays which translates into time saving, efficiency, safety, and more effective clinical results.

A further advantage of the present system and method is that it expands the flexibility and possibilities in control of high frequency generator systems in the clinical setting. It can bring together large bodies of historic or real-time data from imaging, patient records, and past clinical experience, under the interactive control of the surgeon at the time of a specific clinical application. The surgeon can set up his appropriate regime of parameters for the procedure. The surgeon, through the two-dimensional interface, can interact flexibly with the course of the procedure, making decisions about alteration of parameters and cessation of the procedure in a graphic and interactive way. It makes possible experience-based and computer artificial intelligence methods to be applied real time and in graphics display to the user to improve the outcomes for a specific clinical application and patient. Input into the computer and display of experiential data or accumulated stimulation, recording, impedance and generator output information from past patients to compare statistically or directly with those parameter sets associated with a given present procedure can allow complex decisions to be made automatically by the system or in interactive communication with the surgeon in accordance with the present invention.

Yet a further advantage of the present system and method is that it increases the simplicity of the procedure for the operator. A large body of parameters and data can be reduced and assimilated into a simpler form for a specific application, and represented in a simplistic display for him to make decisions and choices as the procedure goes forward.

Figure 10:
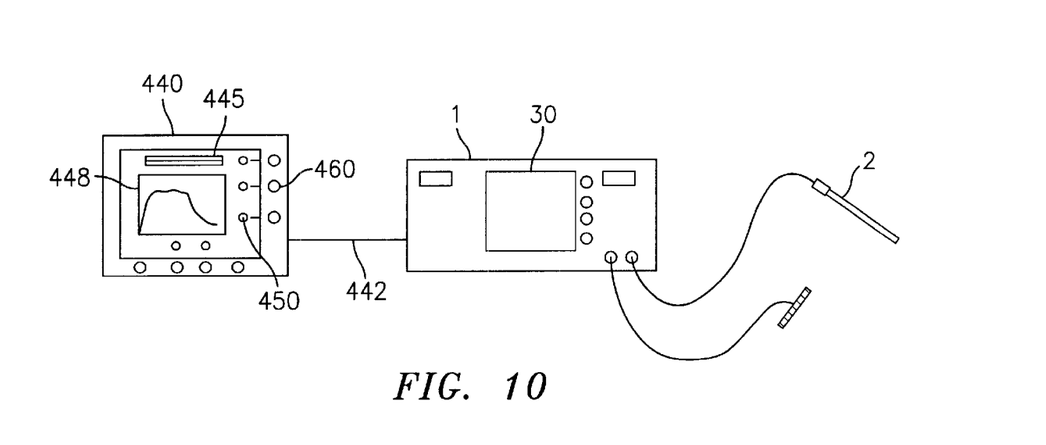
FIG. 10 illustrates another embodiment of the present invention having a two-dimensional interactive screen that is remote from a high frequency generator system.

FIG. 10 shows yet another embodiment of the system according to the present invention in which the two-dimensional display 440 has been separated from the high frequency generator system 1. An electrical, optical, wireless, or electromechanical connection 442 is made between the two-dimensional display 440 and the generator system itself. The display 440 has alphanumeric representations 445, screened icons 450, two-dimensional plotting graphical displays 448, analogous to the examples in the figures described previously. The graphics display 440 may be a slave monitor that displays the same or a condensation or a sub-set of the graphics displays on a secondary monitor 30, which is in the high frequency generator system itself. The monitor 440 can be placed near to the operative site and represent sufficient information and control information for the surgeon to manipulate the controls and interact with the two-dimensional graphics related to the function, status, output parameters, warnings, information output, and stored data in connection with the high frequency generator 1. An advantage of a remote, separated display, as shown in the embodiment of FIG. 10 is that the display can be placed near to the surgeon and to the patient during the operative procedure. The generator system 1 may be elsewhere in the room or in another location altogether. Yet another advantage of the embodiment of FIG. 10 is that in the environment of an open MRI scanner or operative CT or other imaging scanner, it is desirable to have the display near the patient and surgeon during the procedure and the main high frequency generator system 1 at a remote position. Electrical and computer interference of the high frequency generator system may interfere with the imaging process, which makes it desirable to have a high frequency generator system in another room or a sufficient distance away from the imaging machine itself. The remote monitor on user interface 440, however, can be a compact, flat screen, liquid crystal display or other type of two-dimensional graphics display which does not interfere with the operation of an MRI, CT, ultrasound, or other type of scanner and can be located near the operative site.

Further in connection with FIG. 10, the computer graphic, two-dimensional user-interactive interface 440 may have control selector indicated, for example, by button 460. These may be buttons, knobs, push buttons, pressure sensitive switches, raster switches, etc. They may have correspondence to icons on the screen such as 450, which may be selectable lists, menu options, parameters pre-selected or not pre-selected to be chosen by the selector element 460, continuous parameter ranges that can be selected by a knob 460, etc. The user interface screen 440 could be placed on a stand or an arm or by the bedside or operating table. It could be placed near an open MRI magnet and not perturb the magnetic field or imaging characteristics or be perturbed by the magnetic field. This would have the advantage in radiofrequency lesioning procedures or other tissue modification procedures which are being done in or near an MRI imaging machine, in which case the MRI compatible part of the high frequency generator system involving the user interface and control system could be proximate to the surgeon and patient and the MR machine. Examples of LCD two-dimensional displays now exist in commercial industry. By reference, see the two-dimensional, flat-screen display for the OTS Optical Tracking System of Radionics, Inc. (Burlington, Mass.).

Figure 11:
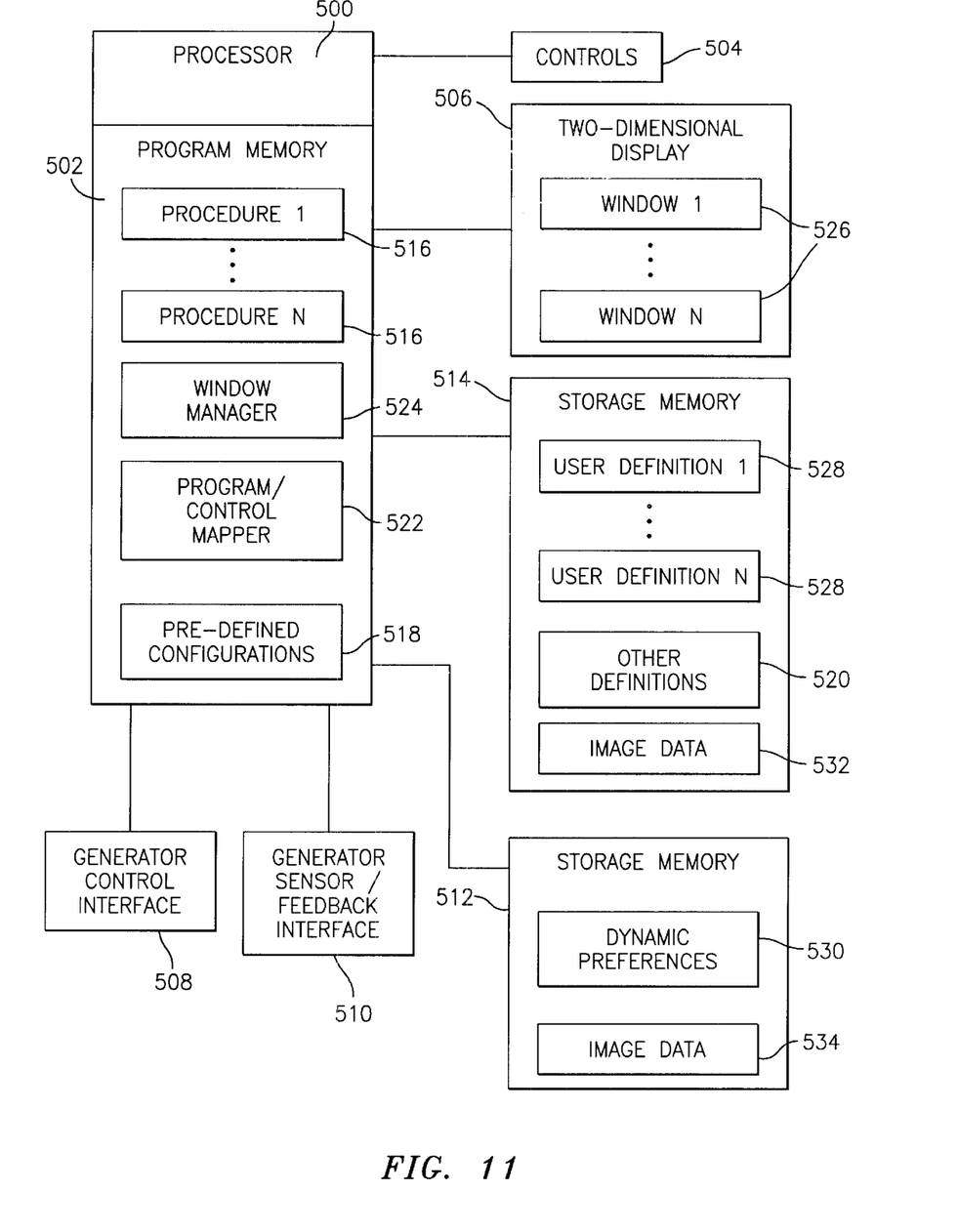
FIG. 11 is a block diagram of processing components, functional components and data components in one embodiment of the invention.

FIG. 11 illustrates processing components, functional components and data components used in one embodiment of the invention. A processor 500 in the high frequency generator system (e.g., in the computer 414, FIG. 9) executes programs stored in a program memory 502 (such as a conventional read only memory "ROM"). The processor 500 processes input signals from the controls 504 associated with the two-dimensional display on the high voltage generator system (e.g., controls 410, FIG. 9). The processor 500 generates display data used to drive a two-dimensional display 506 (e.g., display 448, FIG. 10; display 420 FIG. 9). The processor 500 sends and receives information to and from the generator/sensors via a pair of interfaces 508 and 510. The processor 500 also stores parameters and other information in temporary storage memory 512 (e.g., a conventional random access memory device "RAM") and/or in semi-permanent storage memory 524 (e.g., a conventional flash memory device or a disk drive). These components will be discussed in more detail in conjunction with the operational steps described in FIGS. 12–14.

Figure 12:
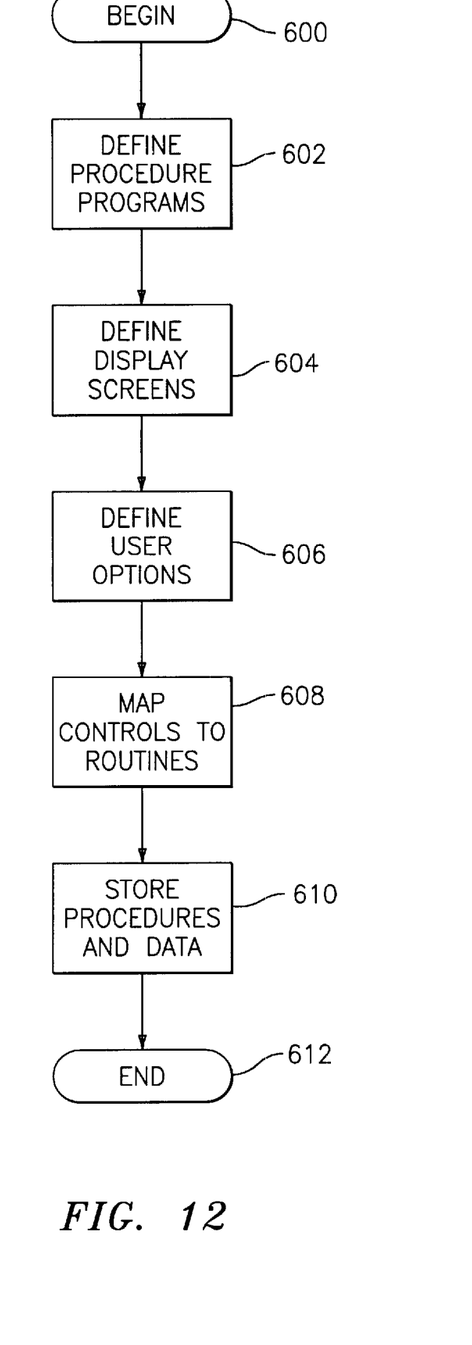
FIG. 12 is a flow chart of a method of programming operational procedures in accordance with one embodiment of the invention.

FIG. 12 illustrates steps that may be used to selectively program the procedures that may be performed by the high frequency generator system, beginning at step 600. Beginning at step 602, the system is configured, for example, at the factory or by an OEM re-seller. This may include, at step 604, defining the procedures that the user wishes the high frequency generator system (e.g., system 1, FIG. 1) to perform and selecting (or writing) the associated program code (e.g., C++). The configuration process also includes defining the various screen layouts to be displayed on the two-dimensional display screen. This may include, for example, defining which icons are used and where they are positioned on the display screen. The configuration process also may include defining options that the user may select when the user operates the system to set up or perform a given procedure (step 606). Next, at step 608, for each program and its corresponding displays, the controls (e.g., 640, FIG. 10) are mapped to the appropriate sub-routines of the program so that when a given control is activated, the corresponding sub-routine will be called. After the system configuration is defined, the associated data is stored in the data memories. For example, programs are stored in the program memory 502, FIG. 11 as represented by procedures 1 through N 516. As used herein, the designation "N" represents an integer that defines the number of corresponding elements (e.g., procedures, definitions, windows) that are used in the system. Configuration data may be stored in one or more of the data memories. Predefined configuration data 518 (e.g., that describes the menus available upon power-up) may be stored in permanent data memory 502. Modifiable configuration data (e.g., user-specific display layouts, associated procedure steps and links to associated programs) may be stored in semi-permanent data memory 514 along with other definition data 520. Information 522 that maps the controls to the sub-routines may be stored in the memory 502. Alternatively, this information may be coded into the programs 516, for example, in the form of interrupt service routines. The procedures in this example then terminate at step 612.

Figure 13:
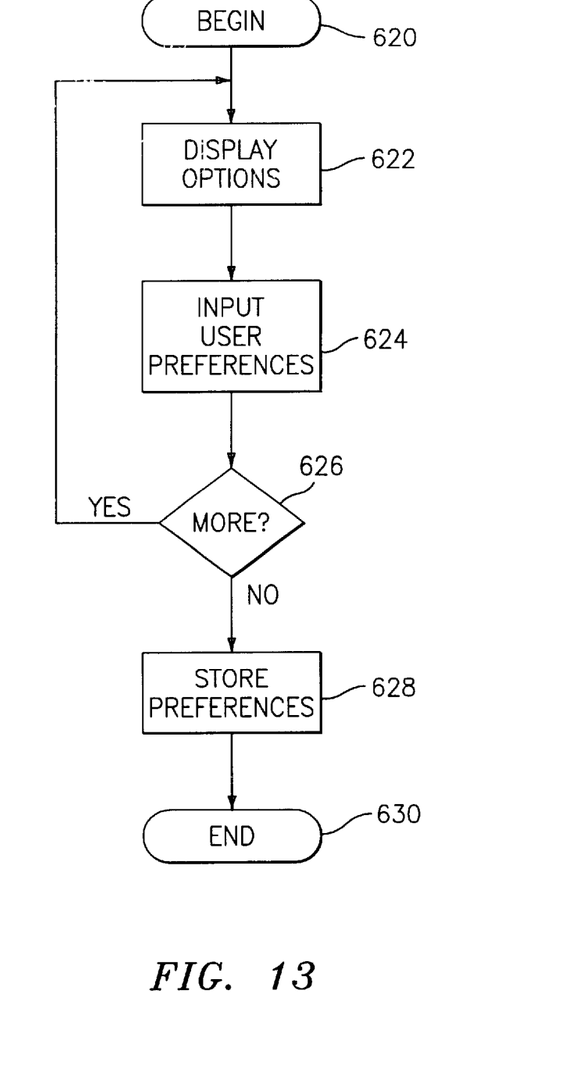
FIG. 13 is a flow chart of a method of programming user defined preferences in accordance with one embodiment of the invention.

FIG. 13 illustrates procedures that enable a user to configure the high voltage generator system and store these preferences in the system, beginning at step 620. At step 622, the system displays a list of available options on the display 506 (FIG. 11). In one embodiment, the menu displayed upon power-up (the main menu) includes a selection that provides an options screen.

From the option screen, the user may define a special procedure such as procedure associated with a particular patient by inputting the appropriate responses (step 624). Here, the user may select which procedures are to be run (e.g., a simple ablation procedure with no feedback, a lesioning procedure with feedback, a stimulation procedure).

The user may select display screen layouts for the procedure (e.g., which icons to use; where they are displayed, which graphs are to be displayed and their associated axis components). The display design procedure may be facilitated by a window manager 524 that enables the user to define multiple windows 526 within the screen of the display 506 and define the information displayed in each window 526. In this respect, the window manager 524 may operate in a similar manner as conventional window design tools that are used in windows-based operating systems.

At step 626, the user is prompted for preferences until the user-specific configuration is complete. Then, at step 628, these preferences are stored in a data memory (e.g., as user preference 1 through N 528 in memory 514). The procedures in this example then terminate at step 630.

Figure 14:
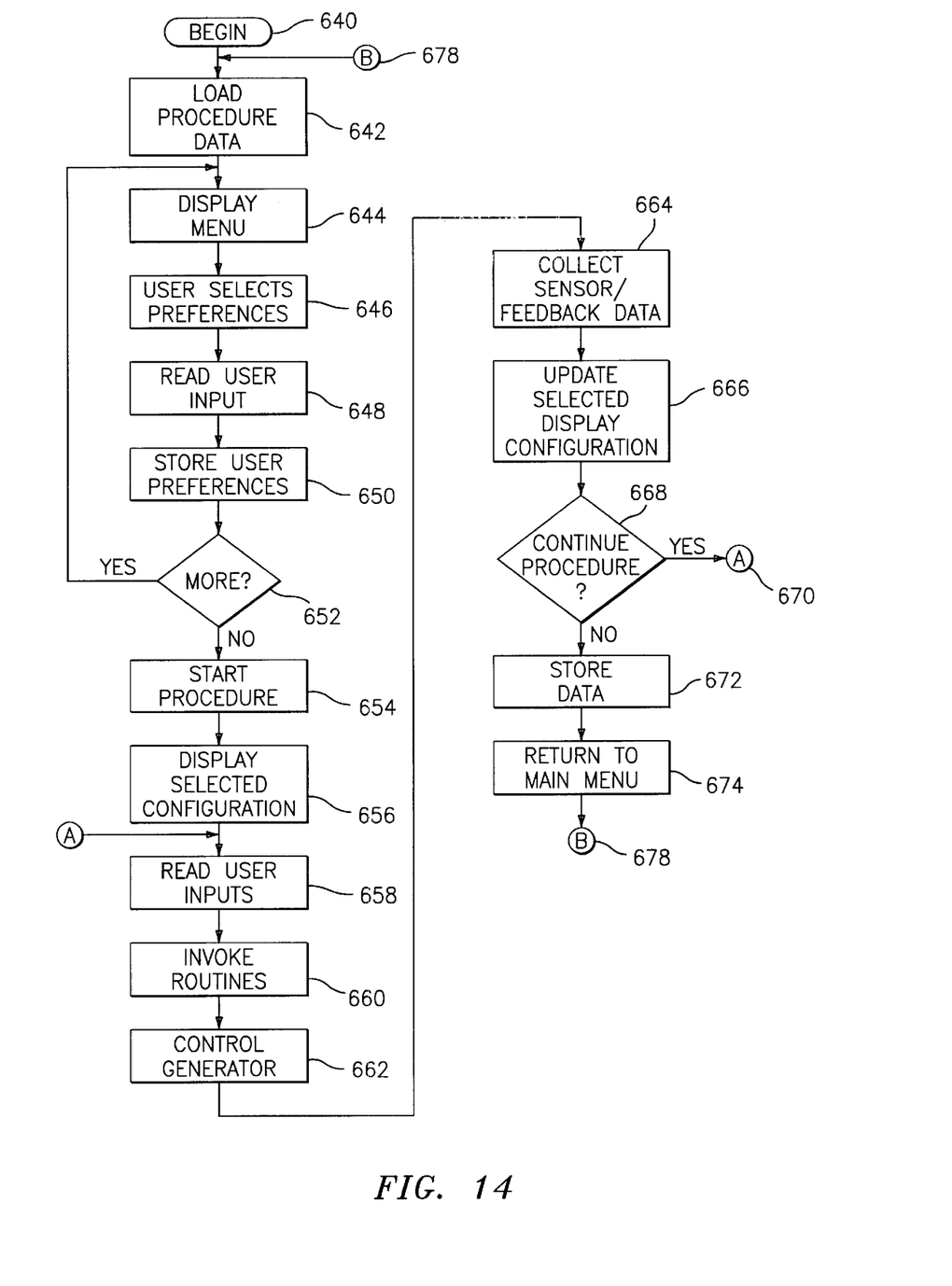
FIG. 14 is a flow chart of a method of performing high frequency generator system procedures in accordance with one embodiment of the invention.

FIG. 14 illustrates operations that may be performed in one embodiment of the invention in conjunction with using the high frequency generator system to perform a procedure on a patient, beginning at step 640. Upon system power-up, the system loads default procedure data (e.g., the processor 500, FIG. 1, executes the default power-up procedure N 516) at step 642.

At step 644 the system displays a menu (e.g., the main menu). This process may involve the invocation of the window manager 524 to display the appropriate windows 526 on the display 506.

In the loop represented by steps 644 through 652, the user may select which procedure is to be run (e.g., a patient-specific procedure) along with any preferences for this session (e.g., power and temperature setting as discussed above). Thus, the user makes his/her selection using, for example, the controls 504 (step 646). The system reads the user's input (step 628) and stores the associated data (step 650), for example, as dynamic preference data 530 in data memory 512.

After all of the preferences have been set up for the selected procedure (step 652), the user starts the procedure by, for example, pressing the control associated with a displayed "start" icon (step 654). The system then displays the first screen for the selected procedure (step 656).

The loop represented by steps 658 through 668 describes several of the steps involved in performing the selected procedure on a patient. This includes scanning the controls 504 for user input during the procedures (step 658) and invoking the corresponding routines (e.g., procedure 1 516, FIG. 11).

At step 662, the system controls the high frequency generator circuits. For example, this includes setting power levels and activation times as described above. In the embodiment of FIG. 10, this step may be accomplished by sending control signals over the line 442 to the generator 1 via an RS-232 interface (represented by interface 508 in FIG. 11) in the display device 440. The interface 508 may include signal conversion (e.g., digital to analog) circuitry, depending on the particular architecture of the system.

At step 664, the system collects sensor, status and/or feedback information from the generator circuits and/or sensors. This data may include periodic temperature or power measurements that may be used to generate the data plots (graphs) discussed above. As shown in FIG. 11, the system may include one or more interfaces 510 for converting the signals from the generator (e.g., RS-232) or the sensor (e.g., analog signals) to digital format.

At step 666, the system updates the display based on, for example, new graph data or particular controls activated by the user. In a similar manner as discussed above, the steps in the loop 658 through 668 may be performed in an order that differs from the order set forth in FIG. 14. For example, the sensors may be sensed at various times before, during or after the procedure.

Once the procedure is complete, any data that is to be saved (such as image data or network data discussed above) is stored in system memory (e.g., image data 532 or 534) or in a device 60 as described above in conjunction with FIG. 1.

Forms and embodiments of the two-dimensional interactive menu display and associated with a high frequency generator system are provided involving various display formats, menus, block diagrams, and procedure steps. However, it should be recognized that other obvious forms may be used and variations of the above illustrative examples given. For example, different menu outputs, procedure steps, graphics display representations, generator actuator elements in conjugation with the two-dimensional menu-driven display can be employed in the system and method without departing from the scope of the invention.

In view of these considerations, as would be apparent by persons skilled in the art, implementations and systems should be considered broadly and with reference to the claims set forth below:

What is claimed is:

1. A high frequency generator system for performing clinical procedures on a patient's body, which comprises:

a high frequency generator adapted for connection to an electrode such that output from said generator can be delivered to body tissue to produce a clinical effect thereon;

processing means for processing and controlling said generator system;

a computer display associated with said processing means and adapted to display graphic and alphanumeric indicia associated with said output of said generator; and a user interface associated with said computer display, said user interface permitting the operator to interactively select and display on said computer display a plurality of menus relating to operation of said generator, and to permit data input within said menus to define selected operating parameters of said generator, to thereby control said output and operation thereof.

2. The system of claim 1 wherein said user interface includes at least one selectable option for control and operation of said generator, said one selectable option being displayed on said computer display.

3. The system of claim 1 wherein said user interface includes selection elements selected from the group consisting of push buttons, level knobs and switches for permitting the data input.

4. The system of claim 1 wherein said user interface is adapted to permit the operator to interactively select for display on said computer display desired graphic and alphanumeric indicia associated with said output of said generator.

5. The system of claim 4 wherein said computer display is adapted to display two-dimensional graphic information based upon output parameters of said output of said generator.

6. The system of claim 5 wherein said computer display is adapted to graphically display a lesion output parameter as a function of time.

* * * * *